United States Patent [19]

De Zaepffel

[11] 4,347,843
[45] Sep. 7, 1982

[54] ILEOSTOMIC BAG

[76] Inventor: Brigitte C. R. De Zaepffel, c/o M.B.S. S.A. 6, bd James Fazy, Geneva, Switzerland, CH-1201

[21] Appl. No.: 172,113

[22] Filed: Jul. 25, 1980

[30] Foreign Application Priority Data

Aug. 8, 1979 [CH] Switzerland ............... 7278/79

[51] Int. Cl.³ .......................................... A61F 5/44
[52] U.S. Cl. ................................................ 128/283
[58] Field of Search ............... 128/283, 294, 295, 272, 128/155, 156

[56] References Cited

U.S. PATENT DOCUMENTS 4,062,451 12/1977 Gander ............................ 128/283

FOREIGN PATENT DOCUMENTS 1277432 6/1972 United Kingdom ............... 128/283
1328764 9/1973 United Kingdom ............... 128/283

Primary Examiner—Kyle L. Howell
Assistant Examiner—T. J. Wallen
Attorney, Agent, or Firm—Joseph G. Kolodny

[57] ABSTRACT

The pocket of the invention comprises a smooth bag (1) fixed at a central aperture of a flexible fixation sheet (2).

The fixation sheet contains one adhesive layer immediately surrounding the aperture and covered by a non-adhesive removable pellicle (9) and another adhesive layer also covered by a non-adhesive removable pellicle (10), concentric to the first one and separated from the first one by an absorbing zone.

Patients can take off pellicle (9) or (10) as they prefer, so that distincts areas of skin are affected each time, avoiding irritation of the skin.

7 Claims, 5 Drawing Figures

ILEOSTOMIC BAG

The present invention concerns a plastic and selfadhesive "ostomic" pocket for ileum, colon or even caecum.

One frequency uses selfadhesive plastic pocket to collect the fecal material melting away from artificial ani. People using this, after having taken off the protective pellicle that covers the sticky film, are able to apply the pocket on the skin surrounding the artificial ano. The sticky layer assures the tightness of the joint between skin and pocket. When the pocket is filled up or when the patient wants to change it for any reason, he must pull it out from the skin and set a new one. Because it is always the same area of skin that is used, it progressively becomes irritated and finally using that kind of pocket becomes painful and even impossible.

It is an object of the present invention to provide an ileostomic bag which avoids these inconveniences of previous ileostomic bags.

It is another object of the present invention to provide an ileostomic bag which is easily applied on or removed from the body of the patients using it.

It is a further object of the invention to provide an ostomic bag which avoids skin irritation or even cures irritated portions of the patient's skin on which the ostomic bag is applied.

Other objects will become obvious from the following disclosure.

According to the present invention, the pockets area of fixation on the skin shows two or more selfadhesive concentric surfaces, that lie down at full length arround the aperture of the entrances material, said concentric surfaces being separated from one another by a non-sticky area, and protected by a removable pellicle of non-adhesive material. The bag of the present invention is thus an ostomic plastic and selfadhesive pocket which comprises a smooth bag of plastic transparent or opaque material fixed arround the aperture of a flexible fixation sheet that bears two concentric zones which are selfadhesive and one of which surrounds immediately the aperture at which the bag is fixed, the other being separated from the first one by a nonadhesive zone which is made of absorbing material. This intermediate zone of absorbing material may contain a bactericide or healing product. Both adhesive layers are each covered by a removable (9, 10) non-adhesive pellicle.

The drawing shows an example of a possible form of the pocket according to the invention.

Figure 4:
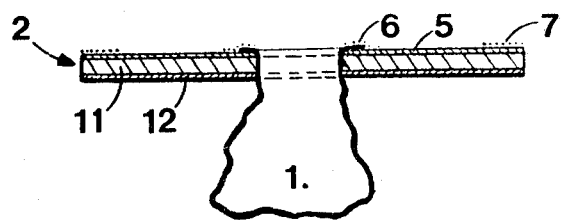
FIG. 4 is a sectional view taken along the axis of the fixing sheet after removal of the non-adhesive pellicles which protect the adhesive zones.

The represented pocket comprises a bag (1) of thin plastic material with its bottom closed by a soldered line. The opening of the bag goes through the central aperture (3) of the smooth fixation sheet (2). The upper edge of the bag opening is folded back on the edge of aperture (3) and is attached on the interior layer (5) of sheet (2). On the face that will be applied on to the skin sheet (2) has two distinct areas of concentric self-adhesive layer (6) and (7) (FIGS. 3 and 4) laying down at full lenghth around aperture (3) (entrance of fecal material) and separated from one another by a non-adhesive area (8). On FIG. 2, one can see these selfadhesive layers still covered by the removable non-sticky pellicles (9) and (10). The sheet of fixation (2) is represented at FIG. 4 with an exagerated thickness to make the drawing clearer. This sheet is made out of many superposed stratum and comprises from the bottom (FIG. 4) a porous voile (5) of fibres for example of absorbing cotton-wool or cotton-wool whose cellulosic fibres, at least the superficial ones have been covered by aluminum or aluminum vapours an absorbing layer of cellulose (11) and an impermeable pellicle (12). The tightness of layer (11) edges is secured by non represented means such, for example, as an impermeable pellicle fold up in a U form and applied on sheet (2) under the selfadhesive layer (7).

The plastic bag and the impermeable sheet can be made out of any polymeric material that is resistant to humidity and impervious to smells and that have the necessary mechanical resistance.

Suitable polymeric material are for example polyethylene, vinylchloride, vinylacetate copolymers, copolymers of vinylidenechloride and the stratified products from these materials for example the stratified foils or laminates of polyvinylacetate or polyethylene with polyvinylchloride and/or polyvinylidene chloride.

Bag and pellicle can be transparent or opaque. Their thickness varies with the material used but is generally between 0,05 and 0,3 mm.

Figure 1:
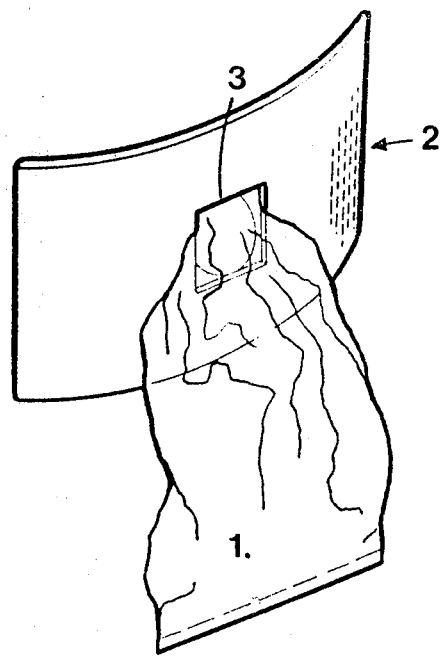
FIG. 1 is a perspective view of an ileostomic pocket showing one embodiment of the present invention.
Figure 2:
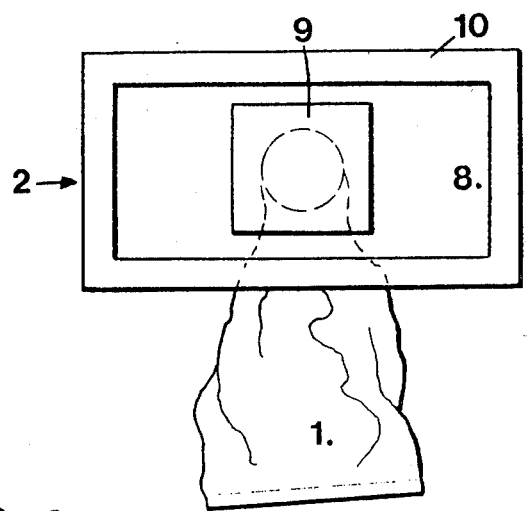
FIG. 2 is a frontal view of the pocket shown in FIG. 1.
Figure 3:
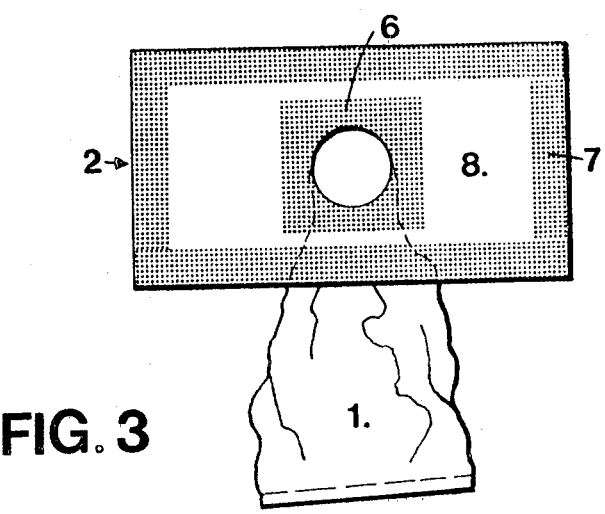
FIG. 3 is a frontal view showing the two selfadhesive zones.
Figure 5:
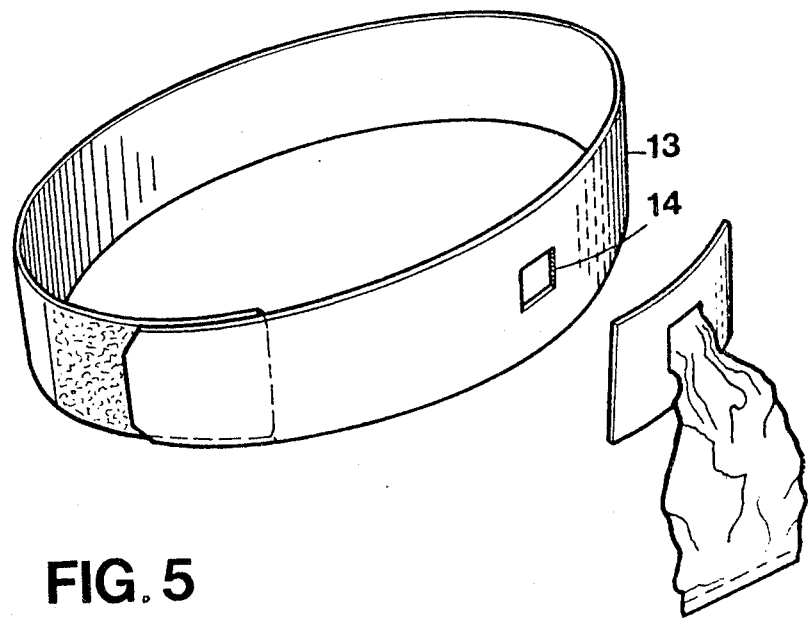
FIG. 5 shows a belt that can be used to maintain the pocket against the abdomen.

The selfadhesive layer can be of rectangular shape as shown in FIGS. 2 and 3. They can also have a circular or an ellipsoidal or even any shape that is proper. The adhesive layers are usually a simple selfadhesive band one face of which sticks to the fixation sheet; the other face is covered by y non-adhesive pellicle (9) or (10) for example by a thin sheet of polyethylene or by silicon paper that protects the adhesive part of the sticky area. It is evident that one prefers a glue having no irritating effect on the skin. The absorbing area lying between both adhesive layers of the pocket according to the present invention is made with fibrous material (wadding or gauze or tulle) that can contain a medical powder or a desinfectant i.e. an antiseptic product or even a product favorising healing or calming irritation of skin.

Excellent results have been obtained with products like "metalline" from LOHMANN KG, that are tissues, felt or non-vowen whose fibres are covered by aluminum or aluminum vapours. Using that kind of ostomic pocket, the patient can take off either pellicle (9) or pellicle (10) and then apply sheet (2) on the skin so that aperture (3) can be just in front of the artificial ano; the selfadhesive area from which he has taken off the covering pellicle sticks on the skin.

When pellicle (9) has been taken off, it is the interior area (6) that is active and the ostomic pocket works as the already known ones.

Taking off pellicle (10) let free the adhesive area (7) that is active and the skin surface immediately surrounding the artificial ano can recover from possible irritation.

In that situation, fluid fecal material will be able to spread between the skin and the fixation sheet up to area (7). But, due to the bactericidal action of the aluminum voile (5) on the one hand and also to the absorbing power of the cellulose layer (11) on the other, that surface of the skin is not affected.

To maintain the pocket against the abdomen of the patient a belt (13) of known type can be used, which has a shutting of rigid hairs like "Velcro" or any other belt fastener made from adequate material. Bag (1) is passed from the interior to the exterior through aperture (14) cut in belt (13) at an appropriate place. Aperture (14) corresponds to aperture (3) of the fixation sheet which is squeezed under the belt against the patient's body when this latter has fastened his belt.

What I claim is:

1. An ostomic, plastic, selfadhesive pocket which comprises a smooth bag of plastic material transparent or opaque, protruding through an aperture made in a fixation sheet and having its opening fixed around the aperture of said sheet (2) that has two adhesive areas, one immediately surrounding the aperture where the bag is fixed and a second one separated from the first one by a non-adhesive zone of absorbing material, both adhesive areas being concentric and covered each by a non-adhesive removable pellicle (9, 10).

2. An ileostomic pocket according to claim 1 having between both adhesive areas an absorbing area of cellulosic fibres.

3. An ileostomic pocket according to claim 1 having between both adhesive areas an absorbing area containing a bactericide product.

4. An ileostomic pocket according to claim 1 having between both adhesive areas an absorbing area containing a healing product together with a bactericide product.

5. An ileostomic pocket according to claim 1 wherein the absorbing area between both adhesive zones is a gauze or a tulle containing an antibiotic, a desinfectant or a medical powder.

6. An ileostomic pocket according to claim 1 wherein the absorbing area consists in cotton-wool or fibrous material, the fibres of which are covered by aluminum.

7. An ileostomic pocket according to claim 1 wherein the adhesive area which immediately surrounds the fixation sheet's aperture is an uninterrupted line or ribbon.

* * * * *